United States Patent [19]
Smith

[11] Patent Number: 5,136,093
[45] Date of Patent: Aug. 4, 1992

[54] QUATERNIZED PANTHENOL COMPOUNDS AND THEIR USE

[76] Inventor: Ronald J. Smith, 504 Wittich Ter., River Vale, N.J. 07675

[21] Appl. No.: 651,205

[22] Filed: Feb. 6, 1991

[51] Int. Cl.$^5$ ............................................. C07C 237/08
[52] U.S. Cl. ..................... 564/197; 424/59; 424/70; 424/71; 424/73; 424/47
[58] Field of Search .................. 424/70; 564/197, 203

[56] References Cited

U.S. PATENT DOCUMENTS

| | | | |
|---|---|---|---|
| 3,230,228 | 1/1966 | Erlemann et al. | 424/70 |
| 3,369,045 | 2/1968 | Erlemann et al. | 424/70 |
| 3,577,528 | 5/1971 | McDonough et al. | 424/70 |
| 3,766,267 | 10/1973 | Zak et al. | 424/70 |
| 4,220,167 | 9/1980 | Newell | 424/70 |
| 4,444,750 | 4/1984 | Green et al. | 424/70 |
| 4,610,874 | 9/1986 | Matravers | 424/70 |
| 4,631,187 | 12/1986 | Padden et al. | 424/70 |
| 4,725,433 | 2/1988 | Matravers | 424/70 |
| 4,764,306 | 8/1988 | Login | 424/70 |
| 4,891,214 | 1/1990 | Stevens et al. | 424/70 |
| 4,897,262 | 1/1990 | Nandagiri et al. | 424/71 |
| 4,922,642 | 5/1990 | Rutzen et al. | 424/70 |
| 4,940,785 | 7/1990 | Stober et al. | 424/70 |
| 4,950,468 | 8/1990 | Nakamura et al. | 424/70 |

*Primary Examiner*—Carolyn Elmore
*Attorney, Agent, or Firm*—Weingram & Zall

[57] ABSTRACT

Quaternized panthenol compounds of the formula:

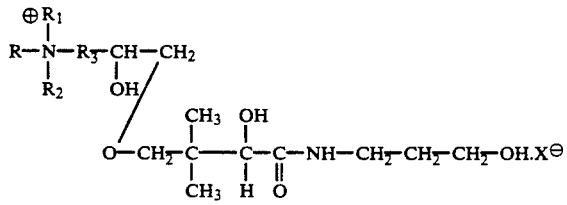

wherein R, $R_1$ and $R_2$ are alkyl and $R_3$ is alkylene, each independently, straight or branched chain of 1-24 carbon atoms, and X is a halogen.

6 Claims, No Drawings

QUATERNIZED PANTHENOL COMPOUNDS AND THEIR USE

BACKGROUND OF THE INVENTION

1. Field Of the Invention

This invention relates to functional ingredients for cosmetic products, in particular quaternized panthenol compounds having enhanced substantivity in cosmetic products.

2. Prior Art

Hair and skin conditioners are functional materials, which are used to improve the appearance and manageability of human hair and the appearance of skin. Contained in such products are cationic compounds, e.g. surfactants, polymers. These compounds provide substantivity of the compositions to hair and skin due to the attachment thereto by means of chemical bonds. For example, following treatment with hair rinses and conditioning shampoos containing such cationic compounds hair is easier to comb when wet without tangling and there is less "fly-away" when it is combed dry. Moreover it is softer, smoother, has more gloss, and appears to have more body. In the case of skin conditioners, which often incorporate cationic resins, rinsing with water does not appreciably remove them from the skin.

There are a large number of cationic compounds on the market with applications in personal care products. Panthenol is one of these well known compounds suitable for incorporation into cosmetic formulations. Panthenol is a stable, biologically active form of pantothenic acid. Panthenol has been incorporated into a number of well-known commercial cosmetic and pharmaceutical products with cosmetic and therapeutic effects, for example, creams, hair grooming liquids, lipsticks, aftershave lotions, and aerosol hair sprays, see Rubin, Magid & Scheiner, "Panthenol in Cosmetics", Proc. Sci. Sec. TGA, 32:6 (1959).

It is also well-known in the art that cationic quaternary ammonium compounds are effective ingredients in hair conditioning preparations. They are believed to be effective because they possess a positive electrostatic charge, which is attracted by and neutralizes the negative charges of hair protein. The mutual attraction of opposite electrostatic charges thus causes the quaternary ammonium compound to remain on the hair. This tendency to remain on the hair is termed substantivity. Substantive quaternary ammonium compounds not only neutralize the electrostatic charges of hair, but can also provide lubricity, by virtue of long chain (fatty) substituents within such compounds.

Other relevant art includes the following U.S. Patents:

| | |
|---|---|
| 3,230,228 | ERLEMANN ET AL |
| 3,577,528 | McDONOUGH ET AL |
| 3,766,267 | ZAK ET AL |
| 4,444,750 | GREEN ET AL |
| 4,631,187 | PADDEN ET AL |
| 4,764,306 | LOGIN |
| 4,891,214 | STEVENS ET AL |
| 4,923,642 | RUTZEN ET AL |
| 4,940,785 | STOBER ET AL |
| 4,950,468 | NAKAMURA ET AL |

U.S. Pat. No. 3,230,228 to Erlemann et al discloses panthenol ethers and thioethers of a specific formula. Note that at column 1, lines 51-59 the compounds can be converted into an acid addition or quaternary salt if desired.

U.S. Pat. No. 3,577,528 to McDonough et al discloses hair conditioner compositions containing quaternary ammonium compounds containing 15 or more total carbon atoms (column 2, lines 29-38). A preferred quaternary ammonium compound is stearyl dimethyl benzyl ammonium chloride.

U.S. Pat. No. 3,766,267 to Zak et al discloses compositions consisting of quaternary halides of trialkyl or hydroxyalkyl amino alkyl gluconamides which show high substantivity for keratinaceous substances. Attention is directed to the formula at the top of column 2, wherein R can be methyl, R' may be $C_1$ to $C_{12}$ alkyl, n is an integer from 2 to 4.

U.S. Pat. No. 4,444,750 to Green et al discloses hair conditioners which are linear polymeric quaternary ammonium materials.

U.S. Pat. No. 4,631,187 to Padden et al discloses hair care products containing a quaternary compound having one erucic group, i.e. a mixed alkenyl having at least about 65% $C_{22}$ olefins derived from erucics, cis-13-docosenoic acid.

U.S. Pat. No. 4,764,306 to Logan describes a process for preparing certain bis-quaternary ammonium compounds and mixtures thereof. Note the formula in the middle of columns 3 and 4.

U.S. Pat. No. 4,891,214 to Stevens et al discloses a hair conditioning composition comprising quaternary ammonium compounds derived from dimethylaminopropyl amides (column 1, lines 56-64). See, column 1, lines 26-38, which states that quaternary ammonium compounds are used to enhance substantivity.

U.S. Pat. No. 4,923,642 to Rutzen et al discloses quaternary ammonium compounds produced by the reaction of epoxy fatty acid ethers with an alcohol (column 6, lines 24-46).

U.S. Pat. No. 4,940,785 to Stober et al discloses a method for preparing cellulose ethers containing quaternary nitrogen by reacting cellulose with QUAB (2,3-epoxypropyltrimethyl ammonium chloride) (column 4, lines 51-63), i.e. see formulas in Abstract and the top of column 2. These modified cellulose products are used in cosmetics (hair treatment), in textiles (softener, antistatic agents), in the paper industry, in flotation and flocculation and in drilling fluids.

U.S. Pat. No. 4,950,468 to Nakamura et al discloses a hair treating composition containing stearyltrimethyl ammonium chloride (column 2, lines 53-56).

The following U.S. Patents teach the use of panthenol in hair care products:

U.S. Pat. No. 4,220,167 to Newell:
U.S. Pat. No. 4,610,874 to Matravers;
U.S. Pat. No. 4,897,262 to Nandaqiri et al; and
U.S. Pat. No. 4,725,433 to Matravers.

Newell at column 4, lines 13-16 discloses a "pantothenyl alcohol" in a hair composition.

U.S. Pat. No. 4,610,874 to Matravers discloses the use of panthenol in a hair conditioner product.

Nandagiri et al at column 4, line 30 describes the use of panthenol in a non-aerosol hair spray composition.

U.S. Pat. No. 4,725,433 to Matravers discloses the use of panthenol in a hair care product. Further at column 2, lines 45-49, this patent discloses polymeric quaternary ammonium salt of hydroxyethylcellulose reacted with trimethyl/ammonium substituted epoxide (CTFA name: Polyquaternium 10) in a hair conditioner.

Manufacturing Chemist, July 1987, Alexander "Cationic Polymers for Skin & Hair Conditioning", describes polymers for skin and hair conditioning products as well as several techniques used to demonstrate the substantivity of these polymers on hair and skin, including the "Rubine dye tests".

Alexander also describes the reaction of 2,3 epoxypropyl (trimethyl) ammonium chloride with one of the free hydroxy groups of guar gam to produce guar hydroxypropyl trimethyl ammonium chloride having a charge density higher than other guar derivatives. The product commercially known as Jaguar C-13-S from Meyhall Chemical (Celanese), is said to confer conditioning properties to both hair and skin and can be used as a thickener for shampoos, liquid soaps, creme rinses, hand creams and lotions.

None of the aforecited references teach or suggest the quaternized panthenol compounds of this invention and their use in cosmetic product formulations.

OBJECTS AND SUMMARY OF THE INVENTION

It is an object of this invention to provide a functional ingredient for use in cosmetic products, for example, hair styling products, hair care products, personal care products, sun care products, and skin care products.

It is a further object of this invention to provide a quaternized panthenol compound which provides enhanced substantivity to such cosmetic products.

It is a further object of this invention to provide a quaternized panthenol product which has unexpected compatibility with systems containing anionic surfactants, such as in shampoos, soaps, and emulsions.

It is still a further object of this invention to provide a method of enhancing the substantivity of panthenol.

All of the foregoing objects of this invention are achieved by a compound of the formula:

$$\overset{\oplus R_1}{\underset{R_2}{R-N-R_3-CH-CH_2}}\overset{}{\underset{OH}{\mid}}\overset{}{\underset{}{\diagdown}}O-CH_2-\overset{CH_3}{\underset{CH_3}{\overset{\mid}{C}}}-\overset{OH}{\underset{H}{\overset{\mid}{C}}}-\overset{}{\underset{O}{\overset{\mid\mid}{C}}}-NH-CH_2-CH_2-CH_2-OH \cdot X^{\ominus}$$

wherein R, $R_1$ and $R_2$ are alkyl and $R_3$ is alkylene, each independently straight or branched chain of 1-24 carbon atoms and X is halogen. Preferably R, $R_1$ and $R_2$ are methyl and R is methylene or stearyl ($C_{18}H_{37}$) and X is chlorine.

The preferred compounds of this invention are the reaction product of d,l - panthenol and 2, 3 - epoxypropyl stearyl dimethyl ammonium chloride and the reaction product of d,l - panthenol and 2, 3 - epoxypropyl trimethyl ammonium chloride.

These compounds have enhanced substantivity when compared to panthenol and are preferably used in cosmetic products, such as hair styling products, hair care products, personal care products, sun care products, and skin care products.

DETAILED DESCRIPTION OF THE INVENTION

Panthenol (Hoffman La Roche, Inc.; Tri-K Industries, Inc.; R.I.T.A. Corp.) is available in two forms, namely, the dextrorotatory isomer (d - panthenol) or the racemic form (d,l -panthenol). d - panthenol is a colorless, viscous liquid, while d,l-panthenol is a white, crystalline powder. d- and d,l-panthenol are both very soluble in water and alcohol, but are insoluble in fats and oils. Aqueous solutions of d- and d,l-panthenol are most stable in the pH range of 4 to 7, the optimum pH being approximately 6. Hydrolysis occurs at an increasing rate as the pH varies from the optimum pH.

Typical data on the properties of d- and d,l-panthenol are shown in Table I.

TABLE 1

| | Properties of d- and d,l-Panthenol | |
|---|---|---|
| | d-Panthenol | d,l-Panthenol |
| Appearance | Viscous, clear liquid | Crystalline powder |
| Color | None | White |
| Solubility in Water (50%) | Clear, complete | Clear, complete |
| Color of Aqueous Solution | Colorless | Colorless |
| Solubility in Ethanol (50%) | Clear, complete | Clear, complete |

Panthenol can be incorporated into cosmetic formulations without adjustments other than maintaining the pH conditions for the optimum stability of the compound. It may be incorporated directly into the aqueous phase of standard cosmetic preparations or, in the absence of an aqueous phase, intimately dispersed in the oil phase. Cosmetic formulations containing panthenol can be prepared in the usual manner with standard equipment. Likewise, the compounds of this invention can be incorporated in cosmetic formulations.

Panthenol has the formula:

$$\overset{CH_3}{\underset{CH_3}{\overset{\mid}{HOCH_2C}}}\overset{OH}{\underset{H}{\overset{\mid}{-CCONH-CH_2CH_2CH_2OH}}}$$

$C_9H_{19}NO_4$, molecular weight 205.25.

Although it is preferred that the d - or d,l - panthenol compounds or mixtures thereof be utilized as a reactant, however by the use of the term "panthenol" herein it is contemplated that not only these compounds are contemplated but derivatives of panthenol are contemplated as well, for example, the ethers and thioethers of panthenol, see for example U.S. Pat. No. 3,230,228 to Erlemann, the entire disclosure of which is incorporated herein by reference.

The quaternized panthenol compounds of this invention can be derived from both the d-panthenol and d,l-panthenol, although it is preferred to utilize the d,l-panthenol.

The quaternized panthenol compounds of this invention are obtained by reacting a quaternary epoxide with panthenol in an alkaline medium in the presence of water.

The reaction mixture is alkalized by the addition of 1 to 4% by weight of an alkaline metal or alkaline - earth metal hydroxide or oxide, or of an alkaline silicate and/or alkaline aluminate or of a mixture of alkaline hydroxides or oxides or alkaline-earth hydroxides or oxides and alkaline carbonates or the mixture of one or more of these hydroxides, oxides, or carbonates with an alkaline silicate and/or alkaline aluminate.

It is preferred to use from 1 to 3% by weight of an alkaline hydroxide or from 3 to 4% by weight of the alkaline earth hydroxide or oxide in relation to the amount of panthenol in each instance.

The quaternary epoxides or mixtures of epoxides used to react with the panthenol are of the general formula:

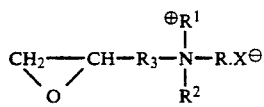

wherein R, $R_1$ and $R_2$ correspond to the same or different alkyl groups and $R_3$ corresponds to alkylene, each branched or straight chained with 1-24 carbon atoms and X is halogen, preferably chlorine. Preferably $R_1$ and $R_2$ are methyl and $R_3$ is methylene and R is methyl ($CH_3$) or stearyl ($C_{18}H_{37}$).

Instead of the quaternary epoxides, the corresponding chlorohydrins can also be used for purposes of the invention in which instance the reaction to form the epoxides corresponding to the above formulas, which react in turn with the panthenol or its derivatives, takes place at the latest in the reaction medium However, in this instance, the stoichiometric amount of alkali for converting the chlorohydrins into the epoxides must be added in addition to a catalytic amount. Panthenol or its derivatives are then added to the reaction mixture.

A neutralization of the final product may be necessary, depending on the application. An inorganic acid, e.g. adipic acid, lactic acid, may be added during the mixing process or after reaction in order to obtain such a neutral product.

The range of the reaction temperature of the process extends from about 5° C. to about 75° C., especially from about 40° C. to 60° C.

The sequence of addition of the reagent to the panthenol in a reaction vessel is not critical.

Preferred commercially available chlorohydrins for producing epoxides for reacting with panthenol are:

Q U A B 188 (Degussa Corp.)

Q U A T 188 (Dow Chemical Corp.)

3-Chloro-2 hydroxypropyl trimethylammonium chloride

Structural Formula:

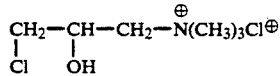

Molecular formula: $C_6H_{15}Cl_2NO$
Molecular weight: 188

Q U A B 342 (Degussa Corp.)

3-Chloro-2-hydroxypropyl-dimethyldodecylammonium chloride

Structural formula:

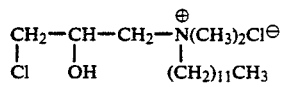

Molecular formula: $C_{17}H_{37}Cl_2NO$
Molecular weight: 342

Q U A B 426 (Degussa Corp.)

3-Chloro-2-hydroxypropyl-N.N.N-dimethyloctadecylammonium chloride

Structural Formula:

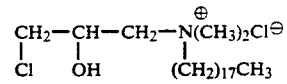

Molecular Formula: $C_{23}H_{49}Cl_2NO$
Molecular Weight: 426

A preferred commercially available quaternary epoxide is:

Q U A B 151 (Degussa Corp.)

Glycidyltrimethylammonium chloride 2, 3-Epoxypropyltrimethylammonium chloride

Structural Formula:

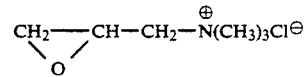

Molecular Formula: $C_6H_{14}Cl\,NO$
Molecular Weight: 151

Some commercially viable and preferred compounds of this invention of the formula:

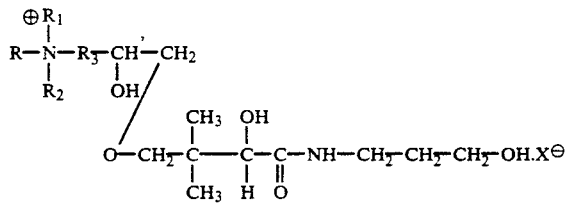

are:

| Panthenol | R | $R_1$ | $R_2$ | $R_3$ | X | Name |
|---|---|---|---|---|---|---|
| d,l | $CH_3$ | $CH_3$ | $CH_3$ | $CH_2$ | Cl | trimethyl quaternized panthenol |
| d,l | $C_{18}H_{37}$ | $CH_3$ | $CH_3$ | $CH_2$ | Cl | stearyl dimethyl quaternized panthenol |
| d,l | $C_{12}H_{25}$ | $CH_3$ | $CH_3$ | $CH_2$ | Cl | lauryl dimethyl quaternized panthenol |
| d | $CH_3$ | $CH_3$ | $CH_3$ | $CH_3$ | Cl | trimethyl quaternized d-panthenol |
| d | $C_{18}H_{37}$ | $CH_3$ | $CH_3$ | $CH_2$ | Cl | stearyl dimethyl quaternized d-panthenol |
| d | $C_{12}H_{25}$ | $CH_3$ | $CH_3$ | $CH_2$ | Cl | lauryl dimethyl quaternized d-panthenol |

The types of compositions or formulations in which the compounds of this invention may be used are:
Hair Styling Products, including:
  Aerosol and Non-Aerosol Mousse
  Aerosol and Non-Aerosol Hair Spray Hair Sculpting (styling) Lotion
Hair Styling Gel
Curl Refresher Lotion
Curl Activators
Hair Care Products, including;
Shampoos
Conditioners
Hair Color, e.g. temporary, semi-permanent and permanent
Permanent Waves
Hair Relaxers
Hair Bleach
Personal Care Products, including;
(a) Bath products, e.g. bubble bath, shower gel, liquid hand soap, facial cleanser, bath soap
(b) Shaving products, e.g. shaving cream, after shave lotion (hydroalcoholic and emulsion based)
Suncare Products, e.g. creams, lotions; and
Skin Care, e.g. creams, lotions, tonics.

The quaternized panthenol compounds of this invention essentially have all of the functional properties of panthenol, with the addition of providing enhanced substantivity to the cosmetic product when compared to panthenol, as well as having enhanced surface activity, enhanced antistatic properties and enhanced lubricity when compared to panthenol. Similar to panthenol, the compounds of this invention can enhance the performance of hair care products, for example, increase the moisture retention of hair, prevent damage to hair during blow drying, reduce the formation of split ends, condition without buildup, and impart sheen and lustre to the hair. Likewise, the compounds of this invention can be quickly absorbed into the skin and hair, and can be ideal for use in aftershaves, colognes, creams, lotions, and suntan products.

In addition to its moisturizing qualities, the compounds of this invention are substantially colorless, odorless, stainless and completely safe. They are freely soluble in water and alcohol and are stable in a critical mutual pH range, making them compatible with other ingredients. Unexpectedly, the compounds of this invention exhibit chemical compatibility with a broad range of anionic compounds commonly used in cosmetic formulations unlike most cationic conditioning agents which are typically incompatible with such anionics. (See, for example, Examples V and X).

It is anticipated that the compounds of this invention when used in hair and skin care products will permit provitamin $B_5$ (panthenol) to be converted to pantothenic acid (vitamin $B_5$) in hair and skin. It is also anticipated that the product will penetrate deeply into the hair shaft, have long lasting moisture control, independent of the atmospheric conditions, prevent over drying of hair and scalp caused by blow dryers, reduce considerably the formation of split ends due to combing and brushing, reduce hair tangling by smoothing the cuticle, provide for clean conditioning without buildup, repair damage caused by chemical and mechanical treatment, e.g. perming, over-processing, combing, brushing and coloring, slow down the aging process (wear and tear of hair) caused by over-shampooing, brushing, and combing (cuticle damage, cortex weakening), increase the tensile strength of hair (especially beneficial to bleached hair), impart sheen and lustre.

Preferred levels of use of the quaternized panthenol of this invention are from about 0.1% to about 20% by weight in the skin care or hair product.

EXAMPLE

In the following Examples, the qualitative test for measuring the substantivity of the compounds on hair was the Rubine Dye Test using Pyrazol Fast Bordeaux, as described in U.S. Pat. No. 3,769,398 to Hewitt and Crawford et al. J. Soc. Cosmet. Chem. 31, 273-278 (1980), the entire disclosures of which are incorporated herein by reference. The intensity of the residual pink color, after rinsing, on a hair swatch previously treated with the compound, is an indication of the degree of deposition of the compound onto the hair. Absence of pink color points to a lack of substantivity.

EXAMPLE I

Trimethyl Quaternized Panthenol

In a one liter reaction flask, fitted with a stirrer, thermometer reflux condenser, heating mantle and a feed funnel, 205 grams of deionized water was charged. 205 grams (1 mole) of d,l-panthenol was charged in the water and stirred until dissolved. In a separate, stirred, one liter vessel, 376 grams (1 mole) of 50% aqueous QUAB 188 (3-Chloro-2-hydroxypropyl trimethylammonium chloride) was reacted with approximately 80 grams (1 mole) of 50% aqueous sodium hydroxide solution, to form a solution of QUAB 151 (2, 3-Epoxypropyl trimethyl ammonium chloride), to a pH of ~9.5. The batch was heated to 50°-60° C., and the QUAB 151 solution was added to the panthenol solution through the feed funnel. The pH of the reaction mixture was checked, and adjusted to ~9.5 with a small additional amount of 50% sodium hydroxide solution, as required. The batch was then agitated at 50°-60° C. for a four hour period to assure complete reaction. The pH of the batch was then adjusted to 6.5-8.0 with a small amount of lactic acid. The resultant product was a clear yellow solution, containing approximately 50% of trimethyl quaternized panthenol. An in vitro efficacy test of this material versus a panthenol solution of comparable concentration, was tested for uptake on human hair swatches and showed an approximate 7% greater uptake than the unquaternized panthenol.

EXAMPLE II

Stearyl Dimethyl Quaternized Panthenol

In a two liter reaction flask, fitted with a stirrer, thermometer, reflux condenser, heating mantle and a feed funnel, 205 grams of deionized water was charged. 205 grams (1 mole) of d,l- panthenol was charged into the water and stirred until dissolved. In a separate stirred one liter vessel, 852 grams (1 mole) of 50% aqueous QUAB 426 (3-Chloro-2-hydroxypropyl stearyl dimethylammonium chloride) was reacted with approximately 80 grams (1 mole) of 50% aqueous sodium hydroxide solution, to form a solution of QUAB 393 (2,3-Epoxypropyl stearyl dimethyl ammonium chloride), to a pH of ~9.5. The batch was heated to 50°-60° C., and the QUAB 393 solution was added to the panthenol solution through the feed funnel. The pH of the reaction mixture was checked, and adjusted to ~9.5 with a small additional amount of 50% sodium hydroxide solution, as required. The batch was then agitated at 50°-60° C. for a four hour period to assure complete reaction. The pH of the batch was then adjusted to 6.5-8.0 with a small amount of lactic acid. The resultant product was a clear yellow solution, containing approximately 50% solids, of which approximately 43% was stearyl dimethyl quaternized panthenol. An in vitro efficacy test of this material versus a 50% panthenol solution was tested for uptake on human hair swatches and showed an approximate 27% greater uptake than the unquaternized panthenol. Adjusting the results for concentration of active material, the stearyl dimethyl quaternized panthenol showed an approximate 31% greater uptake than the unquaternized panthenol.

EXAMPLE III

Substantivity

SAMPLE 1:
Panthenol
50% Aqueous solution.

SAMPLE 2:
Stearyl dimethyl quaternized panthenol, 50% solids Aqueous solution (Example II)

Rubine Dye uptake as a measure of substantivity.

Four tresses of Demeo Natural White Hair weighing approximately 0.5 grams each were immersed in 15 grams of the appropriate solution (i.e. positive control, negative control and test samples) for a period of not less than 5 minutes. Each tress was then rinsed five times with 100 ml of water at 120° F.

The tresses were then immersed in a solution of fast Rubine dye for 15 minutes, rinsed five times with 100 ml of water at 105° F., then air dried overnight on filter paper. Each tress was weighed directly into a tared beaker. The dye was stripped from the hair and the solution then brought to the volume with deionized water. The transmission of each sample was then read at 520 nm and its absorbance adjusted to the weight of the hair sample. The dye concentration was calculated from a standard calibration curve.

Panthenol demonstrated an uptake at a level of 52.35 mg of dye/50 gm of hair; representing a 36.91% uptake with respect to the positive control.

Stearyl dimethyl quaternized panthenol demonstrated an uptake at a level of 66.30 mg of dye/50 gm of hair; representing a 46.74% uptake with respect to the positive control.

Therefore, within the limits of detection imposed by this study, stearyl dimethyl quaternized panthenol (50% solids Aqueous solution), exhibited superior uptake capability by 31% when compared with Panthenol, (50% Aqueous solution), when adjusted for concentration of active material.

FORMULATIONS

EXAMPLE IV

Hair Sculpting Lotion

| C.T.F.A. Name | Ingredients/ Trade Name | % w/w | Function |
| --- | --- | --- | --- |
| Phase A | | | |
| Water | Deionized Water | 86.9 | Solvent |
| PVP | Copolymer 845[1] | 5.0 | Hair Fixative |
| Dimethylaminomethacrylate Copolymer | | | |
| Vinylcaprolactam/ PVP/ Dimethylaminoethylmethacrylate | Gaffix VC-713[1] | 2.0 | Hair Fixative |
| INVENTION | Quaternized panthenol[2] | 1.0 | Hair Conditioner and Detangler Bodying Agent |

| C.T.F.A. Name | Ingredients/ Trade Name | % w/w | Function |
| --- | --- | --- | --- |
| Phase B | | | |
| SD Alcohol 40 | SD Alcohol 40 | 5.0 | Solvent |
| Fragrance | Fragrance E 6367[3] | 0.1 | Fragrance |
| | | 100.00 | |

[1]GAF Chemicals Corporation
[2]Example II herein
[3]Shaw Mudge and Company

Procedure: The water was weighed into a beaker. Each Phase A ingredient was then added to the water phase in the order listed and mixed thoroughly after the addition of each ingredient. The fragrance was dissolved in the alcohol and Phase B was added to Phase A and mixed until clear and uniform.

Properties of Completed Formula:

The product was a clear, pourable liquid styling lotion. The quaternized panthenol was compatible with the hair fixative polymer. The formulation provided excellent wet and dry combing body to the hair and appeared to improve hair curl.

EXAMPLE V

Conditioning Shampoo

| Phase | CTFA Name | Ingredients | % w/w | Function |
| --- | --- | --- | --- | --- |
| A | Water | Deionized Water | 56.95 | Solvent |
| B | Sodium Lauryl Ether Sulfate | Standapol ES-2[1] | 30.00 | Cleanser |
| C | Cetyl Betaine | Tritaine PB[2] | 7.00 | Cleanser |
| | Same | Methylparaben[2] | 0.15 | Preservative |
| | Same | Propylparaben[2] | 0.05 | Preservative |
| | Tetrasodium EDTA | Kelate 220[2] | 0.05 | Chelating Agent |
| D | Cocamide DEA | Standamid KD[1] | 3.00 | Foam Booster |
| E | Imidazolidinyl Urea | Tristat IU[2] | 0.30 | Preservative |
| | Same | Deionized Water | 1.00 | Solvent |
| F | Fragrance | Fragrance E6367[3] | 0.10 | Fragrance |
| G | Same | Citric Acid (50% aq. soln.) | 0.40 | pH Adjuster |
| H | INVENTION | Quaternized panthenol[4] | 1.00 | Hair Conditioner, Hair Bodying Agent |
| | | | 100.00 | |

[1]Henkel Corporation, COSPHA/CD
[2]Tri-K Industries, Inc.
[3]Shaw Mudge and Company
[4]Example II herein Procedure: Phase A was heated to 55° C. Phase B was added and mixed until uniform. Phase C ingredients were added in the order listed and mixed until uniform. When the batch cooled to 45° C., Phase E and Phase F were added and the batch was mixed until uniform. The pH was adjusted with Citric Acid. Phase H was added and the batch was mixed until uniform.

Properties of Complete Formula:

The finished conditioning shampoo was a clear, medium viscosity liquid. The quaternized panthenol (although cationic) was compatible with the anionic surfactants that make up the shampoo. The formation provided improved wet and dry combing, increased body to the hair and better hair curl.

EXAMPLE VI

Leave-On Hair Conditioner

| Phase | C.T.F.A. Name | Ingredient/ Trade Name | % w/w | Function |
|---|---|---|---|---|
| A | Water | Deionized Water | 40.00 | Solvent |
|   | Amodimethicone (and) Tallwtrimonium Chloride (and) Nonoxynol-10 | Siltech E-2145CG[1] | 2.00 | Wet combing; hair conditioner |
| B | Water | Deionized Water | 50.80 | Solvent |
|   | PVP/ Dimethylaminoethylmethacrylate Polycarbamyl Polyglycol Ester | Pecogel GC-310[2] | 1.50 | Hair Fixative |
|   | INVENTION | Quaternized panthenol[3] | 2.00 | Hair Conditioning and Hair Bodying Agent |
| C | Same | Propylene Glycol | 1.25 | Solvent |
|   | Methylparaben | Trisept M[1] | 0.15 | Preservative |
| D | Imidazolidinyl Urea | Tristat IU[1] | 0.30 | Preservative |
|   | Water | Deionized Water | 2.00 | Solvent |
|   |   |   | 100.00 |   |

[1]Tri-K Industries, Inc.
[2]Phoenix Chemical, Inc.
[3]Example II herein

Procedure: The Siltech C-2145CG emulsion was predispersed in the Phase A water in a beaker. The Phase "B" ingredients were dissolved one at a time into the remainder of the water and mixed until clear. Phase "C" ingredients were mixed until clear and uniform. Phase "A" was added to Phase "B" with agitation. Then Phase "C" and "D" were added and the batch was mixed until uniform. The resultant product had an off-white, translucent appearance and was able to be sprayed using a Calmar Mark II High Viscosity Head Yellow orifice spray dispenser.

Properties of Completed Formula:

The finished conditioner was a translucent, off-white liquid that can be applied by spraying through a non-aerosol pump dispenser. The product was left on the hair and did not rinse out. The quaternized panthenol was compatible with the cationic silicone emulsion (Siltech E-2145CG) and with the hair fixative polymer. The formulation provided good conditioning and hair bodying.

EXAMPLE VII

Non-Aerosol Hair Spray

| Phase | C.T.F.A. Name | Ingredients/ Trade Name | % w/w | Function |
|---|---|---|---|---|
| A | SD Alcohol 40 | SD Alcohol 40 | 91.35 | Solvent |
|   | Vinylcaprolactam/PVP/ Dimethylaminoethyl-methacrylate Copolymer | Gaffix VC-713[1] | 8.00 | Hair Fixative |
| B | INVENTION | Quaternized panthenol[2] | 0.50 | Hair Conditioner |
| C | Fragrance | Natural Citrus Bouquet #901219[3] | 0.15 | Fragrance |
|   |   |   | 100.00 |   |

[1]GAF Chemicals Corporation
[2]Example II herein
[3]FlavorScents, Inc.

Procedure: Phase A was weighed into a beaker and was then mixed until clear and uniform. Phase B and then Phase C were added to Phase A while mixing. The batch was mixed until clear and uniform.

Properties of Complete Formula:

The finished hair spray was a clear, pourable liquid that can be sprayed on via a non-aerosol pump dispenser. The quaternized panthenol was compatible with the hair fixative polymer and with the ethanol. The formulation provided conditioning and plasticized the hair fixative polymer.

EXAMPLE VIII

Intensive Hair Conditioner

| Phase | C.T.F.A. Name | Ingredient/ Trade Name | % w/w | Function |
|---|---|---|---|---|
| A | Water | Deionized Water | 67.35 | Solvent |
|   | Polyquaternium-10 | Ucare Polymer JR 30M[1] | 0.50 | Conditioner Thickener |
|   | Methylparaben | Trisetp M[2] | 0.15 | Preservative |
| B | Stearalkonium Chloride | Maquat SC-18 (25%)[3] | 4.00 | Antistat |
|   | Cetrimonium Chloride | Ammonyx Cetac[4] | 4.00 | Detangler |
|   | INVENTION | Quaternized panthenol[5] | 4.00 | Conditioner |
| C | Propylparaben | Trisetp P[2] | 0.10 | Preservative |
|   | Behenamidropropyl-dimethyl-amine Behenate | Catemol 220B[6] | 2.00 | Emulsifier |
|   | Emulsifying Wax NF | T-Wax[2] | 8.00 | Emulsifier |
|   | Cetearyl Alcohol | Cetearyl Alcohol | 3.00 | Thickener |
|   | Avocado Oil | Avocado Oil[2] | 4.00 | Emollient |
|   | Tocopherol | Mixed Tocopherols EM-80[2] | 0.20 | Antioxidant, Vitamin |
| D | Fragrance | Herbal Tea E-8387[7] | 0.20 | Fragrance |
| E | Imidazolidinyl Urea | Tristat IU[2] | 0.50 | Preservative |
|   | Water | Deionized Water | 2.00 | Solvent |
|   |   |   | 100.00 |   |

[1]Amerchol Corporation
[2]Tri-K Industries, Inc.
[3]Mason Chemical Company
[4]Stepan Company
[5]Example II herein
[6]Phoenix Chemical, Inc.
[7]Shaw Mudge and Company Procedure: Ucare Polymer JR was dispersed in the water. After the polymer was dispersed, the Methylparaben was added. Phase A was then heated to 60° C. Phase B was then added to Phase A while mixing. Phase C was heated to 70° C. and then added to Phase AB while mixing with a side sweep agitator. The batch was cooled and mixed to 45° C. and Phase D was added followed by Phase E. The batch was mixed and cooled to 40° C. and poured into jars.

Properties of Complete Formula:

The finished conditioner was a thick, white cream. the formulation was meant to be applied to the hair, left on 5–20 minutes and then rinsed out. The quaternized panthenol was compatible with the other cationic ingredients in the formula. The formulation provided good conditioning and hair bodying especially on damaged, chemically processed (bleached and permed) hair.

EXAMPLE IX

Hand and Body Lotion

| Phase | C.T.F.A. Name | Ingredients/ Trade Name | % w/w | Function |
|---|---|---|---|---|
| A | Water | Distilled Water | 75.35 | Solvent |
| B | Same | Glycerin | 5.00 | Humectant |
|   | Methylparaben | Trisept M | 0.20 | Preservative |
|   | Propylparaben | Trisept P | 0.10 | Preservative |
| C |   | Amigel[1] | 0.40 | Thickener |
| D | INVENTION | Quaternized panthenol[2] | 2.00 | Skin Conditioner |
| E | Emulsifying Wax N.F. Mineral Oil (and) PEG-30 Lanolin (and) | T-Wax[1] | 3.50 | Emulsifier |
|   | Cetyl Alcohol | T Base[1] | 2.00 | Emulsifier |
|   | Same | Avocado Oil[1] | 2.50 | Emollient |
|   | Same | Jojoba Oil[1] | 2.50 | Emollient |
|   | Squalane | Trilane[1] | 5.00 | Emollient |
|   | Dimethicone | Siltech F-350[1] | 0.30 | Emollient |
|   | Tocopheryl Acetate | Vitamin E Acetate[1] | 0.20 | Vitamin |
| F | Same | Phenoxy-ethanol[1] | 0.70 | Preservative |
|   | Fragrance | Fragrance TC-316[3] | 0.25 | Fragrance |
|   |   |   | 100.00 |   |

[1]Tri-K Industries, Inc.
[2]Example II herein
[3]Shaw Mudge and Company

Procedure: Phase A was heated to 75° C. The parabens were dispersed in the glycerin. The amigel was then dispersed into the glycerin. The glycerin mixture was added to the water and mixed vigorously with a propeller. Phase D was then added to water phase. Phase E was heated to 75° C. and added to the water phase with mixing. Mixing was switched to side sweep agitation and the batch was cooled to 45° C. Phase F was then added to the batch. The batch was mixed and cooled to room temperature.

Properties of Completed Formula:

The finished lotion was a white, medium viscosity lotion. The quaternized panthenol was compatible with all of the nonionic ingredients in the formula. The formulation provided skin softening, smoothing and conditioning properties.

EXAMPLE X

NEUTROGENA ™ SOAP BAR

| Phase | Ingredients/Trade Name | % w/w | Function |
|---|---|---|---|
| A | Neutrogena ™ Soap Bar[1] | 98.0 | Soap Bar |
| B | Quaternized panthenol[2] | 2.0 | Skin Conditioner |

[1]Neutrogena Corporation
[2]Example II herein

Phase A was warmed to 72° C., Phase B was added to Phase A with low shear mixing. The batch was cooled slightly and poured into molds. The finished soap bar was a clear, amber solid. The quaternized panthenol was compatible with the anionic soaps and surfactants in the Neutrogena ™ soap bar. Use of quaternized panthenol in the bar improved the lather and provided perceivable skin conditioning benefits as evidenced by the improved after feel of the skin.

I claim:

1. A compound of the formula:

$$\begin{array}{c} \overset{\oplus R_1}{|} \\ R-N-R_3-CH-CH_2 \\ | \quad\quad | \\ R_2 \quad\quad OH \end{array} \quad \begin{array}{c} CH_3 \; OH \\ | \quad | \\ O-CH_2-C-C-C-NH-CH_2-CH_2-CH_2-OH \cdot X^{\ominus} \\ | \quad | \; \| \\ CH_3 \; H \; O \end{array}$$

wherein R, $R_1$ and $R_2$ are alkyl and $R_3$ is alkylene, each independently, straight or branched chain alkyl of 1 to 24 carbon atoms and X is halogen.

2. The compound of claim 1, wherein $R_1$ and $R_2$ are methyl, and $R_3$ is methylene and X is chlorine.

3. The compound of claim 2 wherein R is stearyl.

4. The compound of claim 2, wherein R is lauryl.

5. The compound of claim 1, derived from d-panthenol.

6. The compound of claim 2 wherein R is methyl.

* * * * *